United States Patent
Spahn

(10) Patent No.: US 7,224,770 B2
(45) Date of Patent: May 29, 2007

(54) X-RAY APPARATUS WITH ADAPTED WAITING TIME BETWEEN SUCCESSIVE EXPOSURES

(75) Inventor: Martin Spahn, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 74 days.

(21) Appl. No.: 10/900,797

(22) Filed: Jul. 28, 2004

(65) Prior Publication Data
US 2005/0058251 A1    Mar. 17, 2005

(30) Foreign Application Priority Data
Jul. 28, 2003    (DE) ................ 103 34 395

(51) Int. Cl.
*H05G 1/64* (2006.01)
(52) U.S. Cl. ........................ 378/98.8; 378/91
(58) Field of Classification Search ........... 378/96–97, 378/98.8, 114–117, 91; 250/370.09
See application file for complete search history.

(56) References Cited

U.S. PATENT DOCUMENTS

| | | | | |
|---|---|---|---|---|
| 4,541,106 A | * | 9/1985 | Belanger et al. | 378/98.11 |
| 5,661,774 A | * | 8/1997 | Gordon et al. | 378/101 |
| 6,343,112 B1 | * | 1/2002 | Petrick et al. | 378/98.9 |
| 6,426,997 B1 | | 7/2002 | Fuchs et al. | |
| 6,442,238 B2 | * | 8/2002 | Meulenbrugge | 378/98.8 |
| 6,621,887 B2 | * | 9/2003 | Albagli et al. | 378/42 |
| 6,847,698 B2 | * | 1/2005 | Kaifu et al. | 378/97 |

FOREIGN PATENT DOCUMENTS

| | | |
|---|---|---|
| DE | 137 649 | 9/1979 |
| DE | 36 06 587 | 9/1987 |

OTHER PUBLICATIONS

Hsieh et al., Investigations of a Solid State Detector for Advanced Computer Tomography, IEEE Transactions on Medical Imaging, vol. 19, No. 9, Sep. 2000, p. 930-940.*

* cited by examiner

*Primary Examiner*—Edward J. Glick
*Assistant Examiner*—John M. Corbett
(74) *Attorney, Agent, or Firm*—Schiff Hardin LLP

(57) ABSTRACT

X-ray apparatus has a radiation source operated by a voltage generator, a digital solid-state radiation detector and a control device controlling the operation of the apparatus. The control device determines a waiting time between two successive image acquisitions, dependent on at least one operating parameter for the radiation source set by the control device or by the voltage generator.

8 Claims, 2 Drawing Sheets

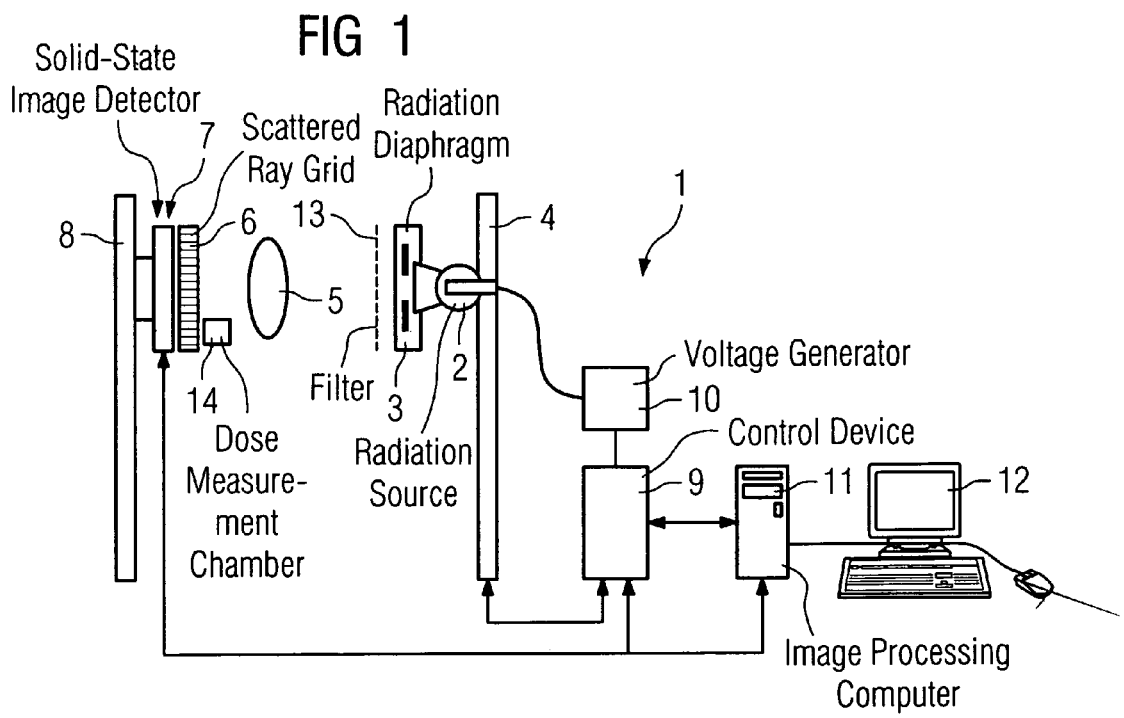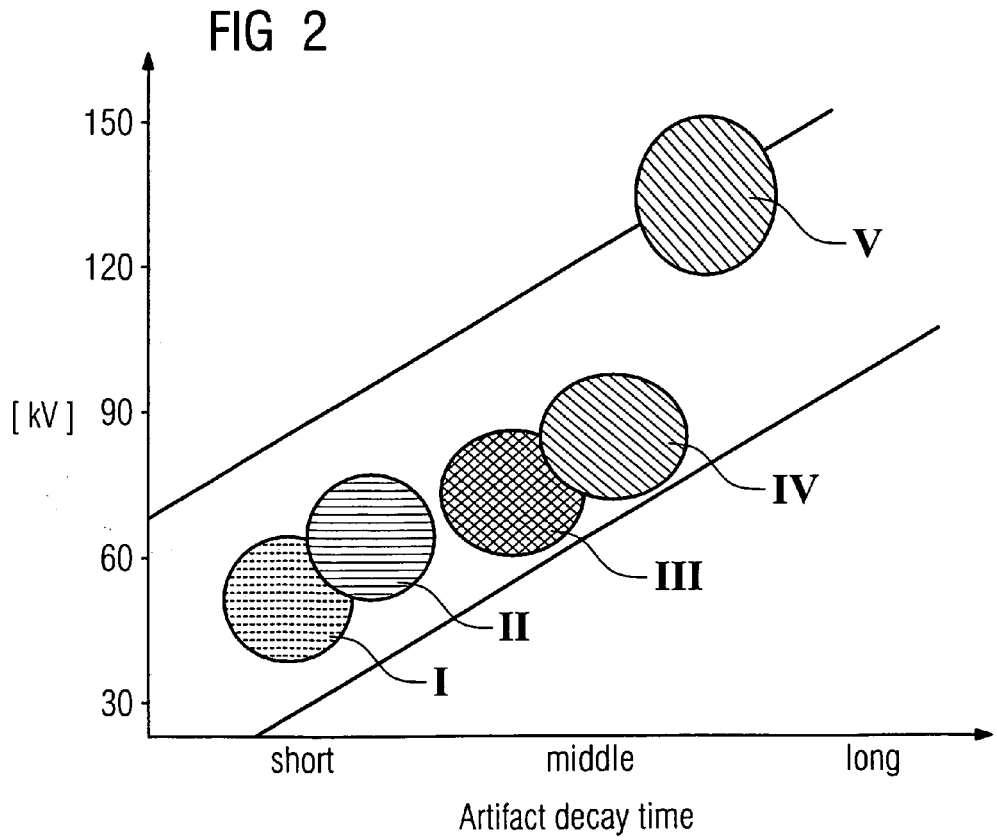

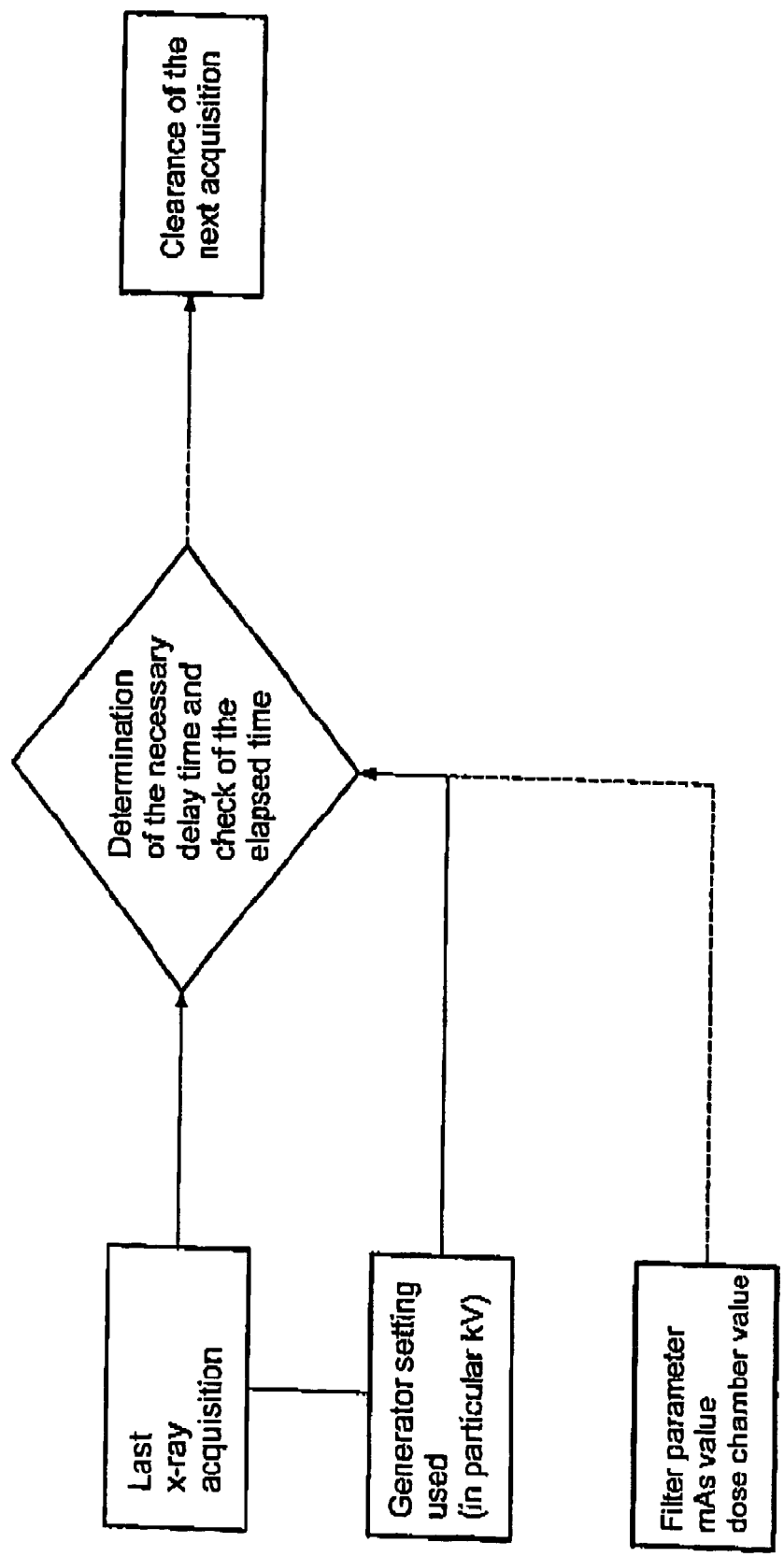

X-RAY APPARATUS WITH ADAPTED WAITING TIME BETWEEN SUCCESSIVE EXPOSURES

BACKGROUND OF THE INVENTION

1. Field of the Invention

The present invention concerns an x-ray apparatus having a radiation source operated by a voltage generator, a digital solid-state radiation detector, and a control device controlling the operation of the apparatus.

2. Description of the Prior Art

In recent years, digital x-ray detectors have changed classical radiography, fluoroscopy, angiography and cardioangiography. Among others, image intensifier camera systems based on television or CCD cameras, storage film systems with integrated or external readout units, systems with optical coupling of the converter foil to CCDs or CMOS chips, selenium-based detectors with electrostatic readout and solid-state detectors with active readout matrices with direct or indirect conversion of the x-ray radiation, represent such digital technologies.

In particular, solid-state detectors play a large role. Such detectors are based on active readout matrices, for example made of amorphous silicon (a-Si). In an x-ray converter (transducer), for example cesium iodide (CsI), the image information is initially converted into light and is subsequently converted into electrical charge in the photodiodes of the matrix and stored there. Related technologies likewise use an active readout matrix made from amorphous silicon, but employ a transducer that generates direct electrical charge (for example, selenium), this charge being subsequently stored on an electrode. In each case, the stored charge is subsequently read out by an active switching element with dedicated electronics and is converted from analog-to-digital form and further processed by the image system.

Planar image detectors based on amorphous materials or semiconductor materials (for example, planar image detectors with indirect conversion by means of a scintillator and a matrix made from amorphous silicon, or detectors with directly-converting materials such as selenium, lead oxide, lead iodide, cadmium telluride) possess physical properties that can lead to ghost image artifacts. Ghost images mean images that contain a persisting signal of an earlier exposure as well as the current signal (an x-ray signal of a patient or another subject, or a dark signal). Among other things, this persisting signal portion significantly adulterates the actual image signal and can lead to a false interpretation of the current image. It is therefore desired to reduce the ghost image signal to a level that can no longer by perceived, and therefore that no longer interferes.

There are in principle a number of possibilities for attempting such a result. A first possibility is the use of a reset light as, for example, is used in planar image detectors made from amorphous silicon. The detector matrix is thereby completely illuminated with light for a short time, and thus the individual charges stored pixel-by-pixel are raised to a uniform level. However, this does not lead to a complete reduction of the artifact. A further possibility is the use of suitable software methods to reduce the artifacts; meaning that they are mathematically "calculated out" in the downstream image processing. In practice, however such model computation has proven to be unsuitable.

SUMMARY OF THE INVENTION

An object of the present invention is to provide an x-ray apparatus that enables an improved image acquisition in terms of an optimally artifact-free exposure.

This object is achieved in accordance with the invention by an x-ray apparatus of the type initially described wherein the control device determines a waiting time between two successive image acquisitions, dependent on at least one operating parameter for the radiation source that is set by the control device or by the voltage generator.

Ghost image artifacts primarily are defined by the radiation dose and the elapsed time. An artifact temporally follows a falling curve, meaning the stored persisting charge, and therewith the ghost image artifact, decays with time. Thus the more time between two exposures, the more that a possible artifact has decayed. Since an artifact appears as a local contrast, it is particularly defined by the subject or organ acquired with the x-ray radiation. In the case of organs such as, for example, the thorax, the pelvis or the lateral spinal column significantly different localized doses are incident on the detector beneath or to the side of the organ. In the regions of the direct radiation (neither shadowed by the organ nor by the radiation diaphragm at the x-ray radiator), dose levels can occur that are higher by a factor of 100 or more than beneath or within the subject or organ. If, for example due to the physical properties of the detector, the ghost image artifact has decayed by a value of 1% after a given time, then the signal value in the directly-irradiated region still always would be as large as the signal beneath the subject in the next exposure.

The possibility exists, however, in every case to wait between two exposures until a possible artifact has decayed, independently of whether an image of the some or a different examination subject is being acquired, and independently of whether a directly radiated region exists, etc. Such a constant waiting time for radiation image exposures of any type, however, is uneconomical.

In accordance with the invention, instead of a waiting time that is constant and the same for all exposure types, a waiting time is determined by the control device, dependent on at least one operating parameter for the radiation source set by the control device or the voltage generator. In particular the operating voltage (thus the kV value and/or the operating current of the radiation source) serves as an operating parameter. This means that the waiting time is defined dependent on the set tube operating parameters, and thus dependent on the generated radiation. When this waiting time has elapsed, the next exposure is enabled. The invention advantageously uses a correlation that exists between the organ to be acquired and the pre-set operating parameter or parameters, in particular the voltage generator data. The likelihood of an artifact is particularly high with organs that are acquired with high kV values. These are precisely the organs that require a high absorption such as, for example, the lungs, the pelvis or the lumbar spine, and in which a large discrepancy generally occurs between the signal values measured by the detector beneath the organ, i.e. in and adjacent the organ (in particular the directly radiated region). For example, while lung exposures are created with 125 kV so that the lung structure behind the ribs also can be detected, the acquisition of the "bony thorax" requires only a tube voltage of approximately 66 kV in order to be able to diagnose the bone structure.

The invention thus achieves an optimization of the waiting time that is unlike conventional techniques, in which a general, maximum "safe" delay time, that is defined for all organs that are examined, must elapse before the system allows the next exposure. Rather, the invention uses the knowledge that different organs lead to ghost image artifacts of different strengths due to the acquisition parameters required for their examination, and therefore the waiting times for these organs can be respectively, different. The type of the organ to be acquired thus is inferred (determined) from the set operating parameters, which in turn is a measure for the possible occurrence of an artifact, the intensity of which is in turn dependent on the dose of the exposure and on the time elapsed after the end of the exposure. From this, a waiting time can be determined that is assigned with regard to the actual exposure conditions of the previous exposure, and thus with regard to the possible actually existing image artifact, rather than with regard to an abstract "maximum" artifact that is based on an exposure-independent wafting time. In this manner, the image acquisition operation can be adapted to the actual exposure conditions, such that an economical generation of the images is possible, but nevertheless a largely artifact-free acquisition operation is achieved.

As described, the operating voltage and/or the operating current of the radiation source can be used as operating parameters for determining the waiting time. Furthermore, the control device that determines the waiting time can do so dependent on at least one other parameter, such as of a filter disposed in the beam path. In x-ray image acquisitions, a filter is frequently disposed in the beam path in order to influence the radiation or the spectrum. The applied dose is thus also influenced, which (as previously stated) is one of the factors that define the intensity of an artifact. If such a filter is not brought into the beam path, this can be taken into account in the determination of the waiting time. It is also possible for the waiting time to be determined dependent on the filter type, the filter material, the filter size or the filter shape.

In an embodiment of the invention, the control device is additionally fashioned to determine the waiting time dependent on a preset value for electrical quantity. Since both the tube current and the exposure time proportionally influence the applied dose, in the acquisition technology the electrical quantity (known as the "mAs product") is set for a subject to be examined. In a circuit known as the "mAs circuit", an exposure control is undertaken with which the tube current is measured and is integrated over the exposure duration after activation of the tube voltage. The mAs product is thereby determined. If this reaches the predetermined mAs value, the tube voltage (and therewith the radiation) is immediately deactivated. This mAs value is thus a measure for the applied dose, and with it a measure for the intensity of a possibly occurring artifact. The electrical quantity value can, in accordance with the invention, likewise be taken into account in the waiting time determination, either exclusively together with an operating parameter of the radiation source or, as necessary, also in connection with the previously specified filter parameter.

As an alternative or in addition to the electrical quantity value, for the waiting time determination a preset value (representing a measure for the applied radiation dose) obtained by a dose measurement chamber disposed in the beam path can be used. Such a dose measurement chamber likewise serves for the time control of the exposure. The dose measurement chamber is located directly in the beam path, and the actual applied dose is determined by it. If the chamber signal reaches a preset value, the exposure is ended. The dose necessary for the desired exposure, which is dependent on the organ to be acquired, also can be defined by the user; a conclusion about this parameter also can be made from the acquired organ, therefore about the occurrence or the intensity of a possible artifact as well, and the waiting time can be determined under still further approximation of the actual properties.

Furthermore, the control device can determine the waiting time dependent on whether the subsequent image acquisition is a radiation image acquisition or a dark image acquisition, thus an offset image. If a further radiation image of the examination subject is acquired after the previous exposure, it should be ensured that the artifact has decayed to the greatest possible extent. If a dark image or offset image is acquired, which is taken into account in the scope of the subsequent processing of one or more previously acquired radiation images, the selected waiting time or decay time can be dependent on how the offset image has been taken into account in the scope of the image processing. If, for example, it only enters at one percent in the scope of the image processing of the previous exposures, it is thus barely notable, thus a large decay is not expected; and the dark image acquisition can ensue relatively quickly. However, if the dark image plays an important role in the scope of the processing, the wait should be longer and a longer decay should be expected.

To determine the most appropriate waiting time for the given situation, it is advantageous to store at least one correlation table with predetermined waiting times in the control device, from which correlation table the waiting time is selected. In the table, waiting times are entered corresponding to the different adjustable operating parameters (for example, the voltage values). Naturally, a number of correlation tables can be provided for additional corresponding parameters, for example the filter or the electrical quantity values or dose chamber values.

The control device can include a timer that is activated with the end of the preceding radiation image acquisition and that detects the passage of the determined waiting time, after which the image acquisition operation is enabled.

DESCRIPTION OF THE DRAWINGS

FIG. 1 is a block diagram showing the basic components of an inventive x-ray apparatus.

FIG. 2 is a diagram representing the dependency between the tube voltage and the artifact decay time.

FIG. 3 is a flowchart showing the determination of the waiting time.

DESCRIPTION OF THE PREFERRED EMBODIMENTS

FIG. 1 shows an inventive x-ray apparatus 1 having a radiation source 2 with a radiation gating diaphragm 3 that, in the exemplary embodiment, are mounted on a stand 4. A subject 5 is exposed to x-ray radiation. The directly transmitted x-ray radiation (radiation not passing through the subject 5) initially is incident on a scattered-ray grid 6 and subsequently on a digital solid-state image detector 7 that is likewise arranged on a stand 8. Furthermore, a filter 13 that can optionally be moved in the beam path and a dose measurement chamber 14 for measuring the applied close are provided.

The control of the overall x-ray apparatus ensues with a control device 9 that controls a voltage generator 10 with which the radiation source 2 is operated. Also provided is an image processing computer 11, with a display such as a monitor 12, to which the acquired images can be output.

The control device 9 determines a waiting time that must elapse between a previous exposure and a subsequent acquisition in order to ensure that a possible artifact resulting from the previous exposure is sufficiently decayed. The determination of the waiting time fundamentally ensues dependent on an operating parameter of the radiation source 2. The decisive criterion represented by this operating parameter is whether and at which intensity an artifact occurs, together with the dose applied. The connection between tube voltage and decay time results in principle from FIG. 2. The tube voltage is plotted in kV along the ordinate; the relative decay time, which is only generally designated here with "short", "middle" and "long", is plotted along the abscissa.

FIG. 2 correlates the tube voltages typical for the respective examinations with typical decay times for ghost image artifacts thereby arising. Shown are five regions I, II, III, IV and V that specify tube voltage ranges that are set to acquire specific body parts or organs. The region I with voltages between approximately 40 kV–65 kV is set for exposures of a hand or a foot. Voltages between approximately 55 kV and 75 kV, as defined by the region II, are set for knee and elbow exposures. A voltage range of approximately 65 kV–85 kV is defined by region III; this is set for shoulder and skull exposures, while the region IV defines a voltage range of approximately 75 kV–95 kV for pelvic exposures. Finally, the region V specifies a voltage range of approximately 11 kV–155 kV for thorax exposures.

Different decay times visibly result at the various examination regions, whereby a quasi-linear connection exists between the height of the tube voltage and the length of the decay time. The greater the voltage, the longer the decay time and vice versa.

After the set generator voltage at which the tube is operated is known to the control device 9, from this it can already roughly determine the decay time of a ghost image artifact, and based on this it can determine a decay (waiting) time, after which a further exposure is allowed. For further refinement and optimization of the determination of the waiting time, it is possible to consider not only the set tube voltage, but also, for example, a parameter associated with the filter 13 that may be disposed in the beam path. The filter 13 (which directly influences the radiation or the spectrum) affect the applied dose and thus the intensity of the artifact. For example, an electricity quantity value serving for the exposure control or a value of the dose chamber 14 likewise serving for the exposure control, both being preset values that would have been set for the preceding exposure, and that likewise have an influence on the intensity of an artifact, can likewise be taken into account.

FIG. 3 is a flowchart showing the determination of the time interval or the waiting time from the voltage generator data of the last radiation image acquisition. As shown, the generator settings used, in particular the kV value or the tube current, are detected in the control device 9, and using these and possible further values (as denoted by the dashed line, such as a filter parameter, the mAs value or a close chamber value), the necessary waiting or delay time is determined.

If the delay time to be adhered to is determined—which already ensues during the creation of the last x-ray exposure—the point in time of the last x-ray exposure is recorded. With the end thereof, a timer (not shown in detail) begins to run that measures the waiting time. Enabling of the next exposure ensues only when the predetermined waiting time dependent on the cited parameters has elapsed.

Although modifications and changes may be suggested by those skilled in the art, it is the intention of the inventor to embody within the patent warranted hereon all changes and modifications as reasonably and properly come within the scope of his contribution to the art.

I claim as my invention:

1. An x-ray apparatus comprising:
   a radiation source;
   a voltage generator connected to said radiation source for setting at least one first parameter for operating said radiation source to emit x-rays;
   a digital solid-state radiation detector disposed to detect said x-rays emitted by said radiation source for a first image acquisition; and
   a control device connected to said voltage generator that controls said voltage generator to set at least one second parameter to operate said radiation source for a second image acquisition by said radiation detector successively following said first image acquisition, said control device also determining a waiting time between said first and second image acquisitions dependent on at least one of said at least one first parameter and said at least one second parameter, using a correlation table stored therein containing predetermined waiting times correlated with said at least one of said at least one first parameter and said at least one second parameter, each predetermined waiting time having a duration that, for said at least one of said at least one first parameter and said at least one second parameter, has been predetermined to at least minimize artifacts in said second image acquisition due to persistence of charge in said radiation detector from said first image acquisition.

2. An x-ray apparatus as claimed in claim 1 wherein said voltage generator sets at least one of an operating voltage and an operating current for said radiation source as said at least one first parameter.

3. An x-ray apparatus as claimed in claim 1 comprising a radiation filter movable into a beam path of said x-rays, and wherein said control device determines said waiting time additionally dependent on whether said filter is disposed in said beam path.

4. An x-ray apparatus as claimed in claim 1 comprising a radiation filter disposed in a beam path of said x-rays, said filter having at least one filter parameter associated therewith, and wherein said control device determines said waiting time additionally dependent on said at least one filter parameter.

5. An x-ray apparatus as claimed in claim 1 wherein said radiation source is operated with a preset electrical quantity value, and wherein said control device determines said waiting time additionally dependent on said preset electrical quantity value.

6. An x-ray apparatus as claimed in claim 1 comprising a dose measurement chamber disposed in a beam path of said x-rays, and wherein said control device determines said waiting time additionally dependent on an applied radiation dose measured by said dose measurement chamber.

7. An x-ray apparatus as claimed in claim 1 wherein said digital solid-state radiation detector is capable of acquiring a radiation image or a dark image as a second of said two successive image acquisitions, and wherein said control device determines said waiting time additionally dependent on whether said second of said two successive image acquisitions is a radiation image or a dark image.

8. An x-ray apparatus as claimed in claim 1 wherein said control device comprises a timer that is activated at an end of a first of said two successive image acquisitions and for detecting passage of said waiting time determined by said control device, and thereafter enables a second of said two successive image acquisitions.

* * * * *